(12) United States Patent
Eden et al.

(10) Patent No.: US 7,745,169 B2
(45) Date of Patent: Jun. 29, 2010

(54) DEVICE AND METHOD FOR THE DETECTION AND ENUMERATION OF MULTIPLE GROUPS OF MICROORGANISMS

(75) Inventors: Gideon Eden, Ann Arbor, MI (US); Ruth Eden, Ann Arbor, MI (US)

(73) Assignee: BioLumix Inc., Ann Arbor, MI (US)

( * ) Notice: Subject to any disclaimer, the term of this patent is extended or adjusted under 35 U.S.C. 154(b) by 0 days.

(21) Appl. No.: 11/766,208

(22) Filed: Jun. 21, 2007

(65) Prior Publication Data

US 2008/0113404 A1    May 15, 2008

Related U.S. Application Data

(60) Provisional application No. 60/857,916, filed on Nov. 10, 2006.

(51) Int. Cl.
 C12Q 1/08   (2006.01)
 C12N 1/02   (2006.01)
 C12M 1/34   (2006.01)

(52) U.S. Cl. ........................ 435/40; 435/34; 435/261; 435/288.7

(58) Field of Classification Search ............... 435/40, 435/261
See application file for complete search history.

(56) References Cited

U.S. PATENT DOCUMENTS

| | | | | |
|---|---|---|---|---|
| 5,266,486 | A * | 11/1993 | Fraatz et al. ............ | 435/288.7 |
| 5,427,920 | A * | 6/1995 | Berndt et al. ............ | 435/34 |
| 6,020,150 | A * | 2/2000 | Contant-Pussard et al. .... | 435/34 |
| 7,041,493 | B2 * | 5/2006 | Rao ...................... | 435/288.1 |
| 2005/0214279 | A1 * | 9/2005 | Silverstein et al. ....... | 424/141.1 |
| 2005/0266516 | A1 * | 12/2005 | Kanipayor et al. .......... | 435/34 |

OTHER PUBLICATIONS

Ruth Firstenberg-Eden, Debra L. Foti, Susan T. McDougal, Jackie Baker. "Optical instrument for the rapid detection of microorganisms in dairy porducts" Elsevier. International Dairy Journal vol. 12 2002 pp. 225-232.*

* cited by examiner

*Primary Examiner*—William H Beisner
*Assistant Examiner*—Michael Hobbs
(74) *Attorney, Agent, or Firm*—Young Basile

(57) ABSTRACT

A device and method simultaneously detects and enumerates two groups of microorganisms in a test sample, utilizing a single test container. In the container liquid growth media, a chromogenic substrate and a fluorogenic substrate are mixed with the test sample. The test container is incubated to allow bacterial growth and metabolism. Spectral changes of the substrates are dynamically detected using two external light sources aimed at a transparent section of the test container, and a single external photo detector. One light source operates in the visible band and the second in the long ultraviolet band. The two dynamic time patterns generated by the two substrates are analyzed in real time to determine the presence or absence of each microorganisms group and to enumerate their original concentrations in the test sample.

13 Claims, 4 Drawing Sheets

DEVICE AND METHOD FOR THE DETECTION AND ENUMERATION OF MULTIPLE GROUPS OF MICROORGANISMS

This patent application claims the benefit of provisional patent application No. 60/857,916 submitted on Nov. 10, 2006.

BACKGROUND

Description of the Prior Art

In samples of water, pharmaceutical, personal care, beverage, food and clinical microbiology, it is desired to provide rapid automated detection and identification of various groups of microorganisms. It is more economical to detect multiple target groups of organisms with a single test container rather than detect every group of microorganisms in a separate test container.

In the last decade, a number of methods have been developed to simultaneously detect coliform and *E. coli* in water and food samples. For example, Edberg (U.S. Pat. Nos. 4,925,789 and 5,429,933) introduced the concept of "nutrient indicator," which not only serves as the primary nutrient source in the medium but which is substantially the only nutrient in the medium that can be metabolized by the target organisms. This nutrient indicator can also change its color or produce a fluorescence signal when metabolized by the target organisms. One target group causes a change in the visible color, whereas the second group causes a change in fluorescence. Chang, et al. (U.S. Pat. Nos. 5,411,867 and 5,643,743) improved the Edberg media by including more nutritious medium ingredients, adding inhibitors, and lowering the pH. Zomer, et al. used a large sample size and developed a device to manually count colonies of coliform and *E. coli*. Coliform were detected by x-gal (color) and *E. coli* by MUG (fluorescence). Brenner (U.S. Pat. No. 6,063,590) reversed the scheme and detected coliform by fluorescence (MUGal) and *E. coli* by color (indoxyl-β-D-glucuronide) with IBDG as an inducer. Their main novelty is the use of Cephalosporin to inhibit Gram—bacteria that are not coliforms.

Boyd (U.S. Pat. No. 5,510,243) described the utilization of inducers to enhance the simultaneous detection of coliform and *E. coli*. He used membrane filtration technology, prior to its introduction on top of a medium containing the chlorophors and florophores, inducers and inhibitors.

The literature describes many fluorescent and chromogenic reactions for specific groups of organisms. All the above methods are used either as presence/absence tests or in conjunction with a plate count method using Petri dishes, filtration apparatus, or MPN counting. These are all manual methods that require a long time to detection and are labor intensive. Isbister (U.S. Pat. No. 5,935,799) describes a semi-quantitative method using a calibration curve. Their method allows for reading color OR fluorescence by the aid of a spectrophotometer. Coliform and *E. coli* are cultured in separate containers as they require two different media. Coliform require succinate in the medium, while succinate is detrimental if present in the *E. coli* medium. Therefore, both assays cannot be combined in one tube. Their method requires a reference tube (control) to accommodate sample color and the reaction of the sample with the media ingredients. For low levels of coliform and *E. coli*, as required for water tests (<1 organism/100 ml) one has to monitor the sample for 12-14 hours. This is not practical as it is longer than a normal work day and very labor intensive. Another system described in the prior art (U.S. Pat. No. 5,432,061) is based upon two detection means—fluorescent carbon dioxide sensor and scattered photon migration device—to enhance the detection of a single group of microorganisms. The carbon dioxide sensor is a discrete matrix element in which a pH indicator is embedded, capable of changing its color when carbon dioxide is detected. The two detection means, however, cannot discriminate growth of more than a single group of microorganisms.

SUMMARY OF THE INVENTION

The new device and method simultaneously detects and enumerates two groups of microorganisms in a test sample, utilizing a single test container. In the container liquid growth media, a chromogenic substrate and a fluorogenic substrate are mixed with the test sample. The test container is incubated to allow bacterial growth and metabolism. Spectral changes of the substrates are dynamically detected using two external light sources aimed at a transparent section of the test container, and a single external photo detector. One light source operates in the visible band and the second in the long ultra-violet band. As an alternative, a single light source generating both bands may be employed. The two dynamic time patterns generated by the two substrates are analyzed in real time to determine the presence or absence of each microorganism group and to enumerate their original concentrations in the test sample.

DEFINITIONS

A chromogen (or chromogenic substrate) is a substance (usually colorless) that, when cleaved by a specific enzyme produced by microorganisms, produces a pigment or dye.

A chromophore is a group on, or part of, a chromogen that produces a color when the chromogen is cleaved by an enzyme.

A fluorogen (or fluorogenic substrate) is a non-fluorescent material that, when cleaved by a specific enzyme produced by microorganisms, produces a fluorescent compound.

A fluorophore is a group on, or part of, a fluorogen that is responsible for the fluorescence when a fluorogen is cleaved by an enzyme.

The term "Primary group of organisms" can refer to a single microbe, a related species of microbes, or a large genus of microbes possessing a common taxonomic characteristic.

The term "Secondary group of organisms" can refer to a single microbe, a related species of microbes, or a large genus of microbes possessing a common taxonomic characteristic.

DESCRIPTION OF THE PREFERRED EMBODIMENT

Figure 1:
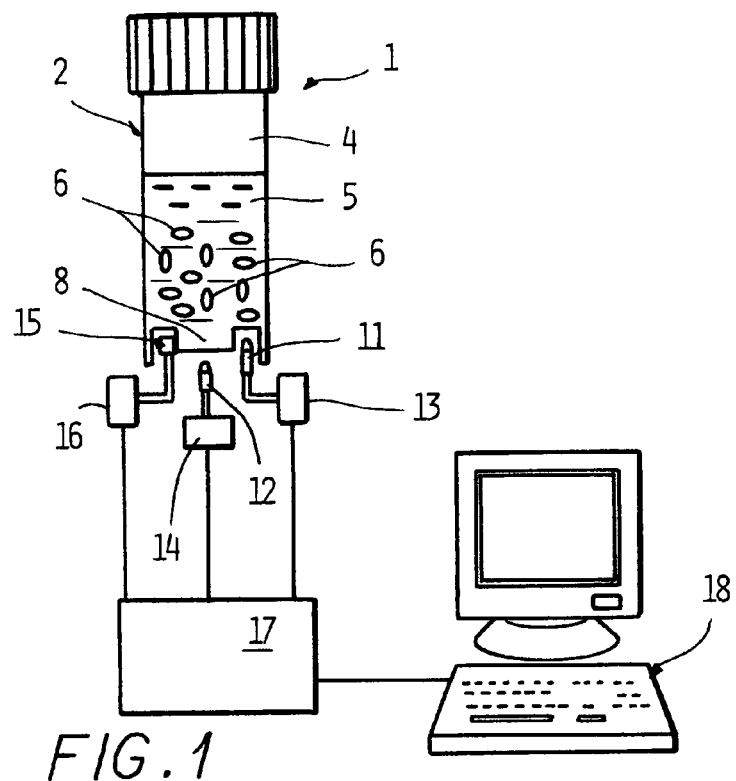
FIG. 1 is a diagram of a preferred embodiment of the device.

FIG. 1 illustrates the device for monitoring the growth of two groups of microorganisms in a sample. The device 1 comprises a container 2 which is transparent to light at least in a window section 8. The container can be made of glass or polymer, transparent to visible light and at least a limited band of the ultraviolet spectrum range. For example, polystyrene can be employed which is transparent to the whole visible spectrum and to the long ultraviolet segment residing above 350 nanometers wavelength. The tested sample 6 is introduced to a liquid mixture 5 comprising media capable of growing the target microorganisms and two substrate indicators, each capable of indicating growth of one of the target groups. In the embodiment, one substrate indicator is chromogenic and therefore can change its color due to growth of the primary group, and the other substrate indicator is fluorogenic and therefore can change its fluorescence characteristic due to growth of the secondary group.

A visible light source 11 and ultraviolet light source 12 are placed interfacing the transparent window 8 filled with the liquid 5. A single photo detector 15 is also placed interfacing the window 8. When either the visible or the ultraviolet light sources are activated, the interaction of light from the source with the substrate indicator is detected by the photo detector 15. In the illustrated embodiment, the photo detector 15 detects the transmission of light from the visible light source 11 through the liquid solution 5, and at 90° therefrom the fluorescent light excited by the ultraviolet source 12. The light sources 11 and 12 are controlled by the electronic controllers 13 and 14, respectively. The light controllers can switch on and off the light sources, determine their intensity and modulate them in predetermined frequencies. A wideband visible light source and optical filter may also be used. The signals detected by the photo detector 15 are amplified and processed by the photo detector processor 16. A central processor 17 controls and synchronizes the operation of the light sources and receives the processed signal from the processor 16. The whole operation can be monitored by a computer 18 that stores the data and provides a user interface, real time data analysis and reports.

The advantage of this embodiment over the prior art is that visible and fluorescence light generated by the system can now be recorded and analyzed dynamically. Instead of observing the changes when the test is over, the system can record the signals repeatedly (e.g., every 10 minutes) and detect immediate changes occurring in the substrates. For larger concentrations of microorganisms, these changes take place faster than those of lower concentrations. Since the processor 17 and the computer 18 analyze these changes in real time, the duration of the tests are shorter than the prior art tests in which human observation is required at specific times (18-24 hours) determined by the maximal incubation time that ensures the detection of the lowest possible bacterial concentration.

Figure 2:
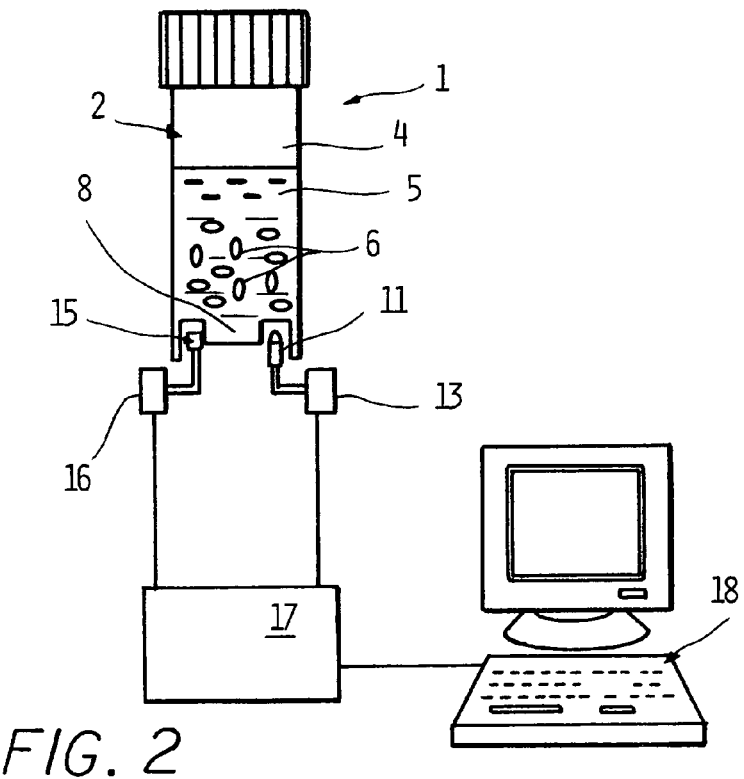
FIG. 2 is a diagram of an alternative embodiment of the device.

FIG. 2 illustrates another embodiment for monitoring the growth of two groups of microorganisms in a sample. The device 1 comprises a container 2 which is transparent to light, at least in a window section 8. Similar to the first embodiment, the container can be made of glass or polymer, transparent to visible light and at least a limited band of the ultraviolet spectrum range. For example, polystyrene can be employed which is transparent to the whole visible spectrum and to long ultraviolet segment residing above 350 nanometers. The tested sample 6 is introduced to a liquid mixture 5 comprising media capable of growing the target microorganisms and two substrate indicators, each capable of indicating growth of one of the target groups. Similar to the previous embodiment, one substrate indicator is chromogenic and therefore can change its color due to growth of the primary group, and the other substrate indicator is fluorogenic and therefore can change its fluorescence characteristic due to growth of the secondary group.

Unlike the first embodiment, there is no separate visible light source. A single light source 11 is placed interfacing the transparent window 8 filled with the liquid 5. A single photo detector 15 is also placed interfacing the window 8. The light source 11 is a wide spectral band source covering both ultraviolet and a portion of the visible spectrum. For example, a gas discharge tube can cover the long UV range, but also a limited visible range that appears in the violet-blue range. When the combined visible and ultraviolet light source is activated, the interaction of light from the source with the substrate indicator is detected by the photo detector 15. In the illustrated embodiment, the photo detector 15 detects the transmission of visible light and the fluorescent light excited by the combined source 11. The light source 11 is controlled by the electronic controller 13. The electronic controller 13 can switch on and off the light source, determine its intensity and modulate it in predetermined frequencies. The signal detected by the photo detector 15 is amplified and processed by the photo detector processor 16. The central processor 17 controls the operation of the light source and receives the processed signal from the processor 16. The whole operation can be monitored by a computer 18 that stores the data and provides user interface, real time data analysis and reports. In this embodiment, it is preferable that the dynamic direction of the interaction light of the visible spectral band, corresponding to growth of the primary group of microorganisms, is opposite to the direction of the fluorescent reaction light due to growth of the secondary group of microorganisms. For example, this embodiment can be used for a combined coliform/*E. coli* test using a mixture of ONPG color reaction changing from clear to yellow during coliform growth and fluorescent MUG increasing its fluorescence indicating *E. coli* growth. Using the system illustrated in FIG. 2, the color change results in a decrease of the signal detected by the photo detector 15, while the increase in fluorescence results in the increase of the detected signal. Consequently, the combined curve is capable of indicating individual growth of the two groups, avoiding the necessity for two light sources.

Many different combinations of primary and secondary groups of organisms can be monitored simultaneously in the system. The system requires that one of the groups of organisms changes the fluorescence due to its growth, while the second group changes the color in the container due to its metabolism. For example, a combination of gram negative bacteria (GNB) and *E. coli* can be monitored by the inclusion of a dye indicator in the medium of an L-alanine aminopeptidase for GNB and β glucoronidase dye indicator for the detection of *E. coli*. For GNB, a color indicator, such as β-napthalamide-β-L-alanine (color change from colorless to purple), can be used. Alternatively, a fluorescent dye, such as 4-methylumbelliferyl-β-L-alanine, can be used. For *E. coli*, a color indicator, such as β-D-glucuronide (color change from colorless to purple), can be used. Alternatively, a fluorescent dye, such as 4-methylumbelliferyl-β-D-glucuronide, can be used. Similarly, a method for the detection of all gram positive bacteria and *Staphylococcus aureus* can be developed by the utilization of 4-methylumbelliferyl phosphate in conjunction with GNB inhibitors and/or antibioitics. *S. aureus* can be detected by the use of dye indicator orthonitrophenyl phosphate.

For purposes of enumeration of primary and secondary groups of microorganisms simultaneously, the Detection Time for each time sequence in which the difference between a predetermined number of consecutive data points in the sequence data changes to follow the growth pattern of the corresponding microorganisms is determined. Then the number of each of the groups of microorganisms in the sample is evaluated by applying the equation:

$$CFU = \log^{-1}\left(\log\frac{C_{si}\ln 2}{K_B t_g} - \frac{\log 2}{t_g}(t_D - t_L)\right)$$

wherein:
CFU is the colony forming units;
log denotes the 10 base logarithmic function;
ln denotes the natural logarithmic function;
$C_{si}$ is the initial concentration of the corresponding indicator substrate modifying reagents;
$K_B$ is the bacterial activity;
$t_g$ is the bacterial generation time;
$t_D$ is said Detection Time; and
$t_L$ is the time duration of the lag phase.

EXAMPLE

A medium containing: tryptophan 1.5 g/l; ammonium sulfate 2.5 g/l; sodium lauryl sulfate 0.3 g/l; Sodium desoxycholate 0.05 g/l; bile salts 0.4 g/l; sodium chloride 2.5 g/l; magnesium sulfate 0.1 g/l; O-nitrophenyl-β-D-galactopyranoside (ONPG) 0.1 g/l; isopropyl-β-D-thiogalactopyranoside (IPTG) 0.1 g/l; 4-methylumbelliferyl-β-D-glucoronidase (MUG) 0.1 g/l was used for the simultaneous detection of coliform and *E. coli*.

Figure 3:
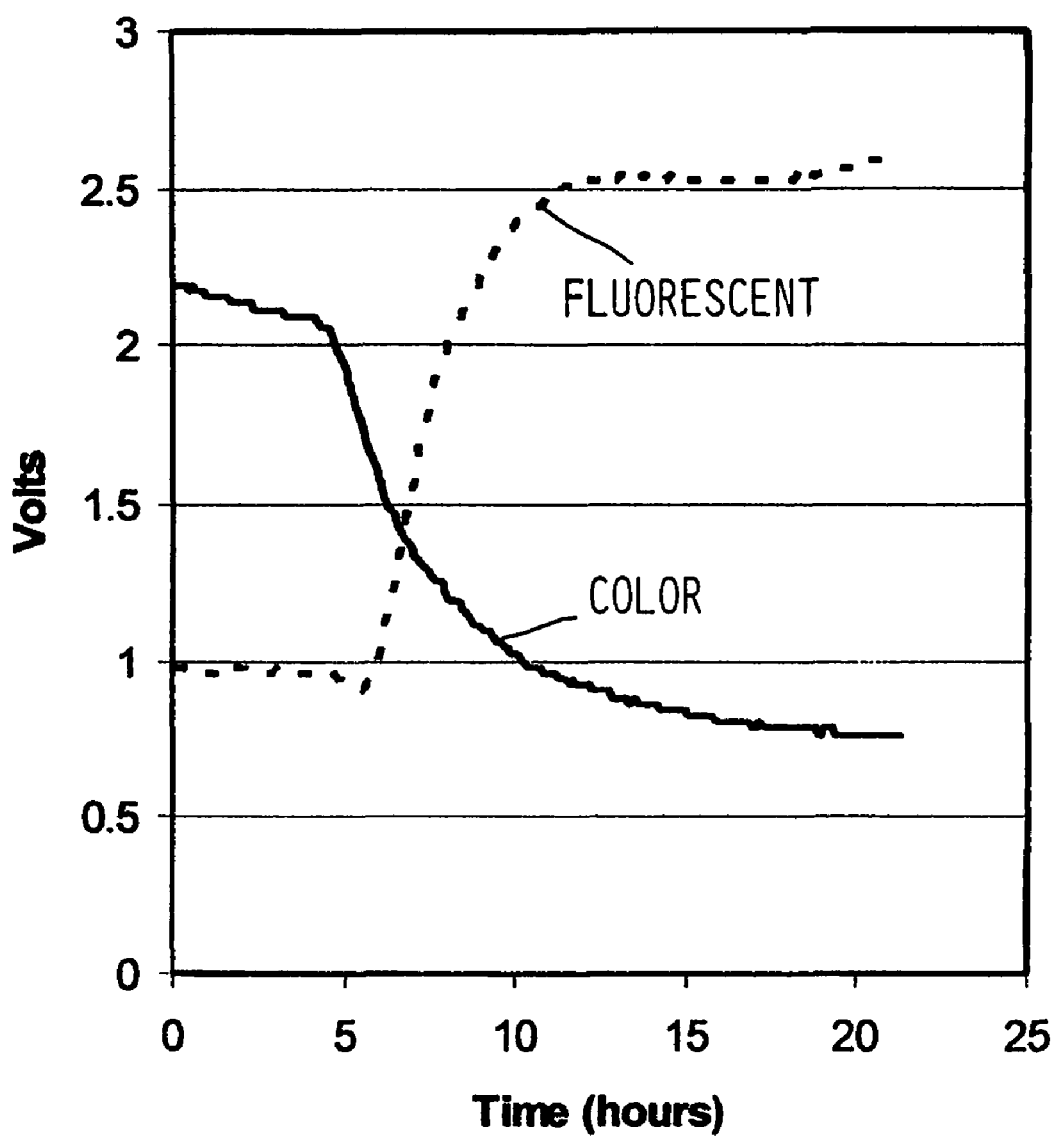
FIG. 3 is a chart of a plot of the experimental data for water inoculated with *E. coli*.
Figure 4:
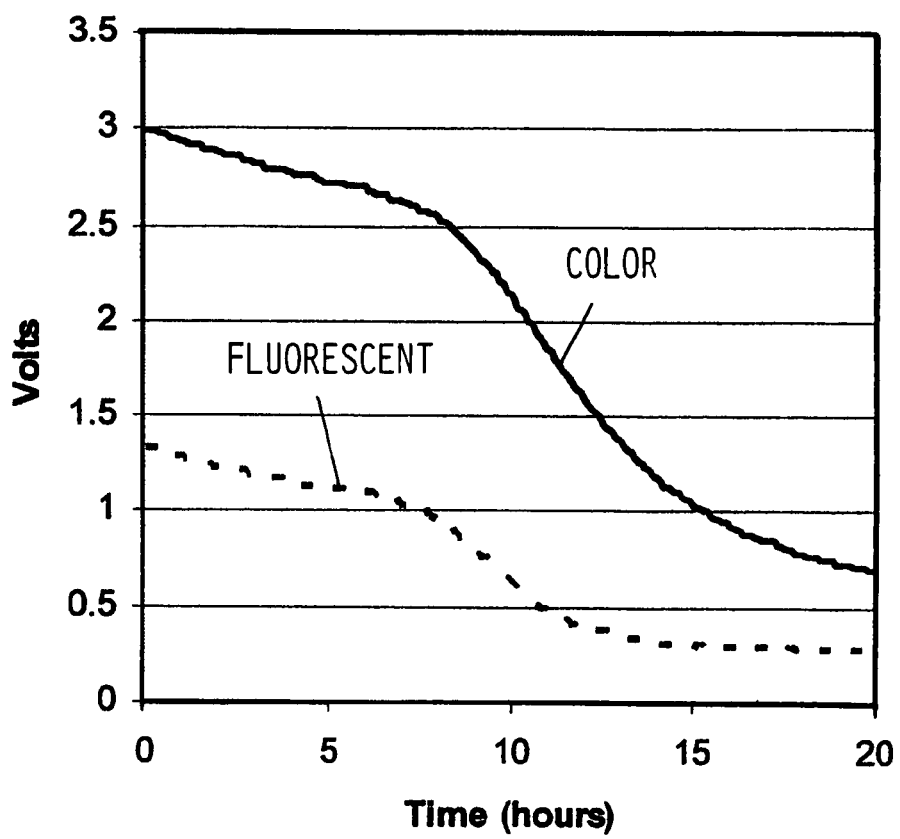
FIG. 4 is a chart of a plot of the experimental data for water inoculated with *Enterobacter aerogenes*.
Figure 5:
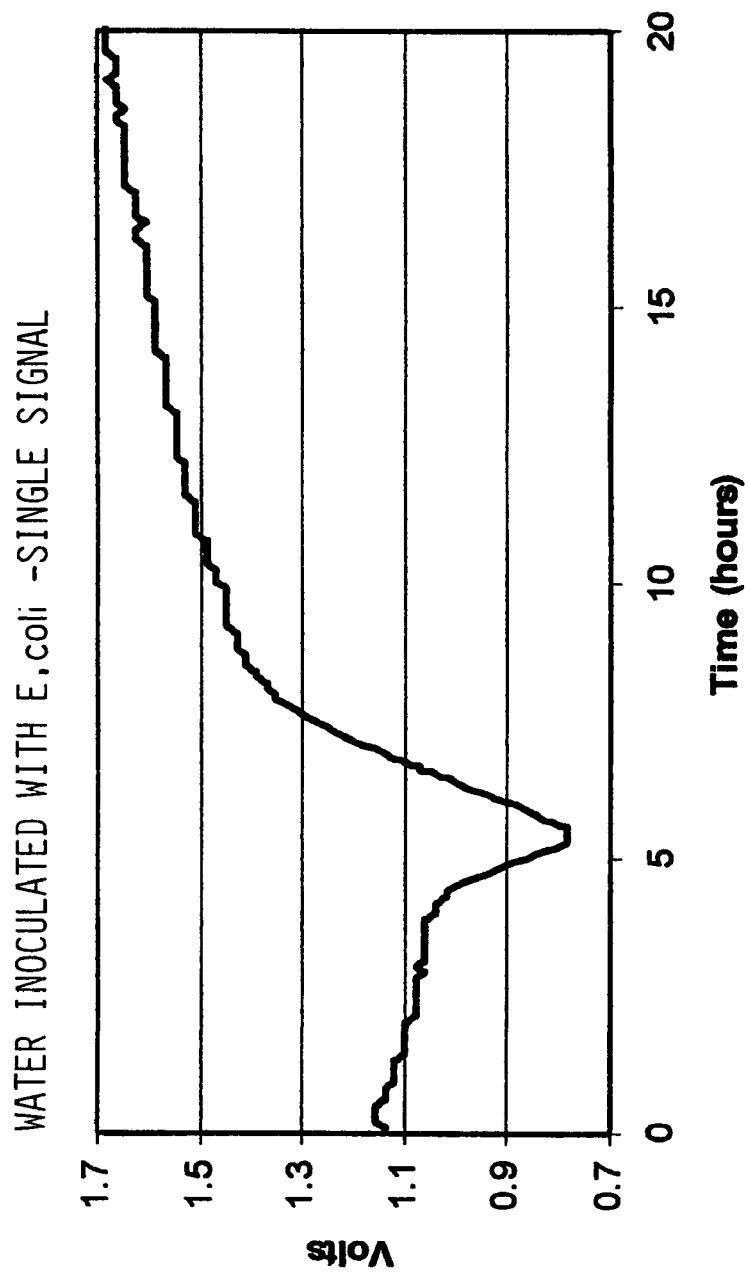
FIG. 5 is a chart of a plot of the experimental data for water inoculated with *E. coli* using the device of FIG. 2.

100 ml of test water was combined with the dehydrated medium to obtain the final concentrations listed above and inserted into a container with a window, as described above. The color and fluorescence were monitored automatically every 10 minutes. A flat curve was obtained in water that did not contain either coliform or *E. coli*. FIG. 3 shows the curve obtained with water inoculated with *E. coli*. The color signal starts going down in a rapid rate due to the creation of the yellow color after around 6 hours. The fluorescent signal starts a sharp upward trend around 7 hours due to the formation of the UV signal. FIG. 4 shows the curves obtained with the coliform *Enterobacter aerogenes*. There is only a decrease in the curves due to the color formation, and no fluorescence is observed. FIG. 5 shows the curve obtained for *E. coli* with the single light source associated with the embodiment of FIG. 2.

The invention claimed is:
1. A test kit for selectively and simultaneously detecting the presence of primary and secondary groups of microorganisms in a test sample, the test kit comprising:
a container configured to receive the test sample, the container made of material transparent to visible light and ultraviolet light in a specific spectral band;
a mixture of materials contained in said container, the mixture of materials including growth media compounded to promote growth of both the primary and secondary groups of microorganisms, a chromogenic substrate material capable of selectively indicating growth of the primary groups of microorganisms, and a fluorogenic substrate material capable of selectively indicating growth of the secondary group of microorganisms; and
a photo reader, the photo reader consisting of:
a visible light source generating electromagnetic energy directed through said transparent material of the container, the visible light source interacting with said chromogenic substrate to yield chromogenic interaction light indicative of growth of the primary groups of microorganisms;
an ultraviolet light source generating electromagnetic energy directed through said transparent material and interacting with said fluorogenic substrate to yield fluorogenic interaction light indicative of growth of the secondary groups of microorganisms; and a single photo detector, capable of detecting said chromogenic interaction light and fluorogenic interaction light and producing detection signals respective to said chromogenic interaction light and said fluorogenic interaction light; and
a controller electronically connected to the visible light source associated with the container, the ultraviolet light source associated with the container, and the single photo detector, the controller configured to switch the respective light sources on and off in a sequential order;
wherein said chromogenic and fluorogenic substrates are selected to enable the fluorogenic substrate to indicate the growth of the secondary group of microorganisms while the primary group of microorganisms is simultaneously growing and changing the color of said chromogenic substrate.

2. The device of claim 1 wherein said visible light source comprises a wideband light source and an optical filter limiting the energy generated by said wideband light source to said specific band in the visible spectrum.

3. The device of claim 2 wherein said wideband light source is an incandescent lamp.

4. The device of claim 1 wherein said visible light source is a light emitting diode.

5. The device of claim 1 wherein said ultraviolet light source is one of an ultraviolet light emitting diode or a gas discharge lamp.

6. The device of claim 1 wherein said photo detector is one of a photo diode, a phototransistor, and a photon multiplying tube (PMT).

7. The test kit of claim 1 wherein said photo detector and said visible ultraviolet light sources are positioned such that electromagnetic energy of said visible light source passes through said mixture directly to the photo detector in a straight line, and the electromagnetic energy of said ultraviolet light is generated at an angle relative to said straight light, yielding fluorogenic interaction light passing indirectly to the photo detector.

8. The test kit of claim 7 wherein said angle is a 90° angle.

9. A method for monitoring the growth of primary and secondary groups of microorganisms simultaneously growing in a single test sample, comprising the steps of:
introducing a mixture of materials into a container, the mixture of materials including a test sample, growth media compounded to promote growth of both the primary and secondary groups of microorganisms potentially present in the test sample, a chromogenic substrate material capable of selectively indicating growth of the primary groups of microorganisms, and a fluorogenic substrate material capable of selectively indicating growth of the secondary group of microorganisms, the container configured to receive the mixture of materials, the container made of material transparent to visible light and ultraviolet light in a specific spectral band, wherein said chromogenic and fluorogenic substrates are selected to enable the fluorogenic substrate to indicate the growth of the secondary group of microorganisms while the primary group of microorganisms is simultaneously growing and changing the color of said chromogenic substrate;

introducing the container containing the introduced mixture of materials into a monitoring device, the monitoring device including;
  A) a photo reader associated with the container, the photo reader consisting of:
    1) a visible light source generating electromagnetic energy directed through said transparent material of the container, the visible light source interacting with said chromogenic substrate to yield chromogenic interaction light indicative of growth of the primary groups of microorganisms;
    2) an ultraviolet light source generating electromagnetic energy directed through said transparent material and interacting with said fluorogenic substrate to yield fluorogenic interaction light indicative of growth of the secondary groups of microorganisms; and
    3) a single photo detector, capable of detecting said chromogenic interaction light and fluorogenic interaction light and producing detection signals respective to said chromogenic interaction light and said fluorogenic interaction light; and
  B) a controller electronically connected to the visible light source, the chromogenic light source and the single photo detector, the controller configured to switch the respective light sources on and off;
switching on the visible light source associated with the photo reader and measuring the intensity of the chromogenic interaction light with the single photo detector;
switching off the visible light, switching on the ultraviolet light source associated with the photo reader, and measuring the intensity of the fluorogenic interaction light with the single photo detector; and
determining the presence of the primary and secondary groups of microorganisms by the intensities of the chromogenic interaction light and the fluorogenic interaction light, respectively.

10. A method for monitoring the growth of primary and secondary groups of microorganisms simultaneously growing in a single test sample, comprising the steps of:
  introducing a mixture of materials into a container, the mixture of materials including a test sample, growth media compounded to promote growth of both the primary and secondary groups of microorganisms potentially present in the test sample, a chromogenic substrate material capable of selectively indicating growth of the primary groups of microorganisms, and a fluorogenic substrate material capable of selectively indicating growth of the secondary group of microorganisms, the container configured to receive the mixture of materials, the container made of material transparent to visible light and ultraviolet light in a specific spectral band, wherein said chromogenic and fluorogenic substrates are selected to enable the fluorogenic substrate to indicate the growth of the secondary group of microorganisms while the primary group of microorganisms is simultaneously growing and changing the color of said chromogenic substrate;
  introducing the container containing the introduced mixture of materials into a monitoring device, the monitoring device including;
    A) a photo reader associated with the container, the photo reader consisting of:
      1) a visible light source generating electromagnetic energy directed through said transparent material of the container, the visible light source interacting with said chromogenic substrate to yield chromogenic interaction light indicative of growth of the primary groups of microorganisms;
      2) an ultraviolet light source generating electromagnetic energy directed through said transparent material and interacting with said fluorogenic substrate to yield fluorogenic interaction light indicative of growth of the secondary groups of microorganisms; and
      3) a single photo detector, capable of detecting said chromogenic interaction light and fluorogenic interaction light and producing detection signals respective to said chromogenic interaction light and said fluorogenic interaction light; and
    B) a controller electronically connected to the visible light source, the chromogenic light source and the single photo detector, the controller configured to switch the respective light sources on and off;
  switching on the visible light source associated with the photo detector and measuring the intensity of the chromogenic interaction light with the single photo detector;
  switching off the visible light source associated with the photo detector, switching on the ultraviolet light source associated with the photo detector;
  measuring the intensity of the fluorogenic interaction light with the single photo detector;
  switching off the ultraviolet light source associated with the photo detector; and
  repeating the preceding steps at predetermined intervals to obtain a recorded time sequence of the chromogenic interaction light and a recorded time sequence of the fluorogenic interaction light for the container.

11. The method of claim 10, including providing real time analysis of the time sequences to resolve the numbers of the primary and the secondary groups of microorganisms in the sample.

12. A method of enumerating primary and secondary groups of microorganisms simultaneously growing in a single test sample by first:
  applying the steps described in claim 10;
  determining the Detection Time for each time sequence in which the difference between a predetermined number of consecutive data points in the sequence data changes to follow the group pattern of the corresponding microorganisms; and
  evaluating the number of each of the groups of microorganisms in the sample by applying the equation:

$$CFU = \log^{-1}\left(\log\frac{C_{si}\ln 2}{K_B t_g} - \frac{\log 2}{t_g}(t_D - t_L)\right)$$

wherein:
CFU is the colony forming units;
log denotes the 10 base logarithmic function;
ln denotes the natural logarithmic function;
$C_{si}$ is the initial concentration of the corresponding indicator substrate modifying reagents;
$K_B$ is the bacterial activity;
$t_g$ is the bacterial generation time;
$t_D$ is said Detection Time; and
$t_L$ is the time duration of the lag phase.

13. The method of claim 12 wherein the coefficients of said equation are determined empirically by performing a statistical best-fit linear regression analysis to derive from experimental data the constants A and B of the equation:

$$\log(CFU) = A - B \cdot t_D$$

wherein said experimental data consists of a multiplicity of tests for different test samples, each consisting of the CFU using the traditional plate counts methodology and the corresponding Detection Time $t_D$.

* * * * *